(12) United States Patent
Terada et al.

(10) Patent No.: US 9,775,342 B2
(45) Date of Patent: Oct. 3, 2017

(54) POWDERY PESTICIDAL COMPOSITION

(75) Inventors: Takatoshi Terada, Osaka (JP); Manabu Tagami, Hyogo (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 1149 days.

(21) Appl. No.: 12/439,701

(22) PCT Filed: Sep. 10, 2007

(86) PCT No.: PCT/JP2007/068007
§ 371 (c)(1),
(2), (4) Date: Mar. 3, 2009

(87) PCT Pub. No.: WO2008/035642
PCT Pub. Date: Mar. 27, 2008

(65) Prior Publication Data
US 2010/0055143 A1    Mar. 4, 2010

(30) Foreign Application Priority Data

Sep. 22, 2006 (JP) ................................ 2006-256918

(51) Int. Cl.
*A01N 25/34* (2006.01)
*A01N 25/08* (2006.01)
*A01N 25/12* (2006.01)
*A01N 25/26* (2006.01)

(52) U.S. Cl.
CPC ............ *A01N 25/12* (2013.01); *A01N 25/08* (2013.01); *A01N 25/26* (2013.01)

(58) Field of Classification Search
CPC .......... A01N 25/26; A01N 25/08; A01N 25/12
See application file for complete search history.

(56) References Cited

U.S. PATENT DOCUMENTS

| 5,030,379 A * | 7/1991 | Knight et al. ................ 510/276 |
| 5,338,551 A | 8/1994 | Lajoie |
| 5,346,704 A | 9/1994 | Lajoie |
| 5,443,835 A * | 8/1995 | Winston ........................ 424/407 |
| 5,583,089 A | 12/1996 | Winston |
| 2002/0054897 A1 * | 5/2002 | Inoue et al. ................... 424/405 |

FOREIGN PATENT DOCUMENTS

| EP | 0847691 | 6/1998 |
| EP | 1 864 573 A1 | 12/2007 |
| JP | 58090502 A * | 5/1983 ............ A01N 25/12 |
| JP | 7-223906 A | 8/1995 |
| JP | 8-99802 A | 4/1996 |
| JP | 11-5704 A | 1/1999 |
| JP | 2002-102680 A | 4/2002 |
| JP | 2002-249402 A | 9/2002 |
| JP | 2003-286106 A | 10/2003 |
| JP | 2003286107 | 10/2003 |
| JP | 2003286108 | 10/2003 |
| JP | 2003286109 | 10/2003 |
| JP | 2005-187462 A | 7/2005 |
| RU | 2229442 C * | 5/2004 |
| WO | 94/00983 A1 | 1/1994 |
| WO | 2006/103827 A1 | 10/2006 |

OTHER PUBLICATIONS

Abdullah et al., Powder Technology, 1999, 151-165.*
Communication for EP Application No. 07807411.9 dated Oct. 18, 2013.
Korean Office Action for Application No. 2009-7005787 dated Oct. 7, 2013.
Office Action for Chinese Application No. 200780034654.4 dated Feb. 5, 2013.
Decision on Rejection for Chinese Patent Application No. 200780034654.4 dated Feb. 19, 2014.
EP Communication for EP 07807411.9 dated Nov. 15, 2012, with Supplementary European Search Report dated Nov. 5, 2012.
Inoue, "Agrochemical Granule", Abstract No. XP-002686290 dated Sep. 6, 2002.
Inoue, Abstract No. XP-002686292 dated Oct. 7, 2003.
Inoue, "Agrochemical Granule", Abstract No. XP-002686293 dated Oct. 7, 2003.
Inoue, "AgroChemical Granule and Method for Producing the Same", Abstract No. XP-002686294 dated Oct. 7, 2003.
Inoue, "AgroChemical Granule and Method for Producing the Same", Abstract No. XP-002686295 dated Oct. 7, 2003.
"Calcium Carbonate Powder", Abstract No. XP-002686291, pp. 1-4, Database: Patent Chemistry, dated Feb. 4, 2006 (retrieved on Oct. 31, 2012).
First Examination Report for Indian Patent Application No. 1623/CHENP/2009 dated Nov. 13, 2014.
Office Action for Brazilian Patent Application No. PI 0717105-6 dated Sep. 3, 2014.

* cited by examiner

*Primary Examiner* — Kyle Purdy
(74) *Attorney, Agent, or Firm* — Sughrue Mion, PLLC

(57) ABSTRACT

Disclosed is a powdery pesticidal composition which comprises a mixture of a coated pesticide comprising a powdery pesticide coated with a thermosetting resin and having a volume median diameter of 10 to 150 μm and a calcium carbonate micropowder having a bulk density of 0.6 g/ml or less, wherein the weight-based ratio of the coated pesticide to the calcium carbonate micropowder is 100:1 to 100:30. The powdery pesticidal composition has good fluidability.

4 Claims, No Drawings

POWDERY PESTICIDAL COMPOSITION

TECHNICAL FIELD

The present invention relates to a powdery pesticidal composition containing a pesticide coated with a thermosetting resin.

BACKGROUND ART

For the purpose of maintaining drug efficacy, alleviating phytotoxicity, or the like, various pesticidal formulations capable of controlled-release of pesticidally active compounds have been proposed. A granular composition comprising a coated pesticidal granule having an average particle diameter of 0.5 mm or more, in which a pesticidal granule containing a pesticidally active compound is coated with a thermosetting resin, and a powdery composition comprising a microcapsule having an average particle diameter of 1 to 50 μm, in which a liquid hydrophobic core substance such as a pesticidally active compound is coated with a thermosetting resin have been known (see JP-A 11-5704 and JP-A 2002-102680).

A powdery pesticidal composition comprising the conventional powdery coated pesticide which is coated with a thermosetting resin has bad flowability, and therefore, when the powdery pesticidal composition is discharged from a container such as a hopper, it may generate bridging or may clog a piping.

DISCLOSURE OF INVENTION

According to the present inventors, good flowabiliy of a powdery pesticidal composition is attained by mixing a particular calcium carbonate micropowder with a powdery coated pesticidal which is coated with a thermosetting resin at a specified ratio to obtain the powdery pesticidal composition. Thus, the present invention includes the following inventions.

[Invention 1]

A powdery pesticidal composition comprising a mixture of a coated pesticide having a volume median diameter of 10 to 150 μm in which a powdery pesticide is coated with a thermosetting resin, and a calcium carbonate micropowder having a bulk density of 0.6 g/ml or less, wherein the weight ratio of the coated pesticide to the calcium carbonate micropowder is in the range of 100:1 to 100:30.

Unless otherwise noted, throughout the specification, the volume median diameter of a powder is measured with a laser diffraction particle size analyzer such as MASTER-SIZER2000 (MALVERN Instruments Ltd.).

[Invention 2]

The powdery pesticidal composition according to the Invention 1, wherein the thermosetting resin is a polyurethane resin and/or a polyurea resin.

[Invention 3]

The powdery pesticidal composition according to the Invention 1 or 2, wherein the bulk density of the calcium carbonate micropowder is in the range of 0.01 to 0.3 g/ml.

[Invention 4]

A method for improving flowability of a powdery coated pesticide which comprises adding a calcium carbonate micropowder having a bulk density of 0.6 g/ml or less to a powdery coated pesticide in which a powdery pesticide is coated with a thermosetting resin, in such an amount that the weight ratio of the powdery coated pesticide and the calcium carbonate micropowder is in the range of 100:1 to 100:30.

In the powdery pesticidal composition of the present invention, the coated pesticide having a volume median diameter of 10 to 150 μm in which a powdery pesticide is coated with a thermosetting resin is a powdery substance formed by agglomerating a powdery pesticide with a thermosetting resin to obtain a core and further coating the core with the thermosetting resin.

Herein, the powdery pesticide may be a powdery pesticidally active compound itself. Usually, the powdery pesticide is a dilution of the pesticidally active compound with a carrier, and the dilution contains 1 to 95% by weight of the pesticidally active compound and 5 to 99% by weight of the carrier, preferably 10 to 90% by weight of the pesticidally active compound and 10 to 90% by weight of the carrier.

The pesticidally active compound used in the present invention is usually in solid form at 20° C., and preferably is also in a solid form at 50° C. Specific examples of the pesticidally active compound include insecticidal compounds, fungicidal compounds, herbicidal compounds, insect growth regulating compounds, plant growth regulating compounds and insect repellent compounds as described below.

Examples of the insecticidal compounds and the insect growth regulating compounds include pyrethroid compounds such as deltamethrin, tralomethrin, acrinathrin and tetramethrin; carbamate compounds such as propoxur, isoprocarb, xylylcarb, metolcarb, XMC, carbaryl, pirimicarb, carbofuran, methomyl and phenoxycarb; organic phosphorus compounds such as acephate, trichlorfon, tetrachlorvinphos, dimethylvinphos, pyridaphenthion, azinphos-ethyl and azinphos-methyl; urea compounds such as diflubenzuron, chlorfluazuron, lufenuron, hexaflumuron, flufenoxuron, flucycloxuron, cyromazine, diafenthiuron, hexythiazox, novalron, teflubenzuron, triflumuron, 4-chloro-2-(2-chloro-2-methylpropyl)-5-(6-iodo-3-pyridylmethoxy) pyridazin-3(2H)-one, 1-(2,6-difluorobenzoyl)-3-[2-fluoro-4-(trifluoromethyl)phenyl]urea, 1-(2,6-difluorobenzoyl)-3-[2-fluoro-4-(1,1,2,3,3,3-hexafluoropropoxy)phenyl]urea, 2-tert-butylimino-3-isopropyl-5-phenyl-3,4,5,6-tetrahydro-2H-1,3,5-thiadiazon-4-one and 1-(2,6-difluorobenzoyl)-3-[2-fluoro-4-(1,1,2,2-tetrafluoroethoxy)phenyl]urea; chloronicotinyl compounds such as imidacloprid, acetamiprid, clothianizine, nitenpyram and diacloden; cartap, buprofezin, thiocyclam, bensultap, phenoxycarb, fenazaquin, fenpyroximate, pyridaben, hydramethylnon, thiodicarb, chlorphenapyr, fenproximate, pymetrozine, pyrimidifen, tebufenozide, tebufenpyrad, triazamate, indoxacarb, sulfluramide, milbemectin, abamectin, boric acid and paradichlorobenzene.

Examples of the fungicidal compounds include benzimidazole compounds such as benomyl, carbendazim, thiabendazole and thiophanate-methyl; phenylcarbamate compounds such as diethofencarb; dicarboximide compounds such as procymidone, iprodione and vinclozolin; azole compounds such as diniconazole, propenazole, epoxiconazole, tebuconazole, difenoconazole, cyproconazole, flusilazole and triadimefon; acylalanine compounds such as metalaxyl; carboxyamide compounds such as furametpyr, mepronil, flutolanil and trifluzamide; organic phosphorus compounds such as tolclophos-methyl, fosetyl-aluminium and pyrazophos; anilinopyrimidine compounds such as pyrimethanil, mepanipyrim and cyprodinil; cyanopyrrole compounds such as fludioxonil and fenpiclonil; antibiotics such as blasticidin S, kasugamycin, polyoxin and validamycin; methoxyacrylate compounds such as azoxystrobin, kresoxim-methyl and methominostrobin; chlorothalonil, manzeb, captan, folpet, tricyclazole, pyroquilon, probenazole, fthalide, cymoxanil, dimethomorph, CGA245704, famoxadone, oxolinic acid, fluazinam, ferimzone, diclocymet, chlobenthiazone, isovaledione, tetrachloroisophthalonitrile, thiophthalimidoxybisphenoxyarsine, 3-iodo-2-propylbutylcarbamate, parahydroxybenzoate ester, sodium dehydroacetate and potassium sorbate.

Examples of the herbicide compounds include triazine compounds such as atrazine and metribuzin; urea compounds such as fluometuron and isoproturon; hydroxybenzonitrile compounds such as bromoxynil and ioxynil; 2,6-dinitroaniline compounds such as pendimethalin and trifluralin; allyloxyalkanoic acid compounds such as 2,4-D, dicamba, fluroxypyr and mecoprop; sulfonylurea compounds such as bensulfuron-methyl, meturfuron-methyl, nicosulfuron, primisulfuron-methyl and cyclosulfamuron; imidazolinone compounds such as imazapyr, imazaquin and imazethapyr; bispyribac Na salt, bisthiobac Na salt, acifluorfen Na salt, sulfentrazone, paraquat, flumetsulam, triflusulfuron-methyl fenoxaprop-p-ethyl, diflufenican, norflurazon, isoxaflutole, glufosinate ammonium, glyphosate, bentazone, mephenacet, propanyl, fluthiamide, flumiclorac pentyl and flumioxazin.

Examples of the plant growth regulating compounds include maleic hydrazide, chlormekat, ethephon, gibberellin, mepikat chloride, thidiazuron, inabenfide, paclobutrazol, and uniconazol.

Examples of the insect repellent compounds include 1S,3R,4R,6R-carane-3,4-diol, and dipropyl 2,5-pyridinedicarboxylate.

The powdery pesticide is usually a micropowder having a volume median diameter of 1 to 100 μm, preferably 1 to 30 μm.

Examples of the thermosetting resin used in the present invention include a polyurethane resin, a polyurea resin, a polyurethane-polyurea resin, and an epoxy resin. Among them, preferred are a polyurethane resin and a polyurea resin, and a polyurethane resin is particularly preferred.

A polyurethane resin is a thermosetting resin made from liquid polyol and liquid polyisocyanate as raw materials, and is obtained by a reaction of polyol and polyisocyanate under heating, for example, at 40 to 100° C. At the same time, if necessary, a curing catalyst such as an organometal or an amine is added.

Examples of the polyol include condensed polyester polyol, polyether polyol, poly(meth)acrylic acid polyol, lactone polyester polyol, polycarbonate polyol, natural polyol and modifications thereof. The condensed polyester polyol is usually obtained by a condensation reaction of polyol and dibasic acid. The polyether polyol is usually obtained by addition-polymerization of propylene oxide or ethylene oxide with polyhydric alcohol or the like. The poly(meth)acrylic acid polyol is usually obtained by a condensation reaction of poly(meth)acrylic acid and polyol, a condensation reaction of (meth)acrylic acid and polyol, or a polymerization reaction of a (meth)acrylic acid ester monomer. The lactone polyester polyol is obtained by a ring-opening polymerization of ε-caprolactone using a polyhydric alcohol as an initiator. The polycarbonate polyol is usually obtained by a reaction of glycol and carbonate. Examples of the polyol include methylene glycol, ethylene glycol, propylene glycol, tetramethylene glycol, hexamethylenediol, trimethylolpropane, polytetramethylene glycol, glycerin, pentaerythritol, sorbitol, sucrose, and oligomers of them. Herein, the poly(meth)acrylic acid refers to polyacrylic acid, polymethacrylic acid or a mixture thereof.

Examples of the polyisocyanate include toluene diisocyanate (TDI), diphenylmethane diisocyanate (MDI), naphthalane diisocyanate, tolylene diisocyanate, hexamethylene diisocyanate, isophorone diisocyanate, xylylene diisocyanate, 4,4-methylene bis(cyclohexylisocyanate), trimethylhexamethylene diisocyanate, 1,3-(isocyanatomethyl) cyclohexane, triphenylmethane triisocyanate, tris (isocyanatophenyl) thiophosphate, and a mixture thereof. In place of the above-described polyisocyanate monomers, their modified forms or oligomers which have flowability may be used. Examples of the modified form of the polyisocyanate monomer include an adduct-modified form, a biuret-modified form, an isocyanurate-modified form, a block-modified form, a prepolymer-modified form, and a dimerized form. Polymethylene polyphenyl isocyanate (polymeric MDI) which is obtained by producing polyamine via condensation of aniline and formalin and then subjecting the polyamine to phosgenation is preferable from the viewpoints that reaction control is easy and that the stream pressure is low and thus workability is excellent.

Examples of the curing catalyst which is used if necessary include organometals such as dibutyltin diacetate, dibutyltin dichloride, dibutyltin dilaurate, dibutylthiostannic acid, stannous octanoate, and di-n-octyltin dilaurate; triethylenediamine, N-methylmorpholine, N,N-dimethyldidodecylamine, N-dodecylmorpholine, N,N-dimethylcyclohexylamine, N-ethylmorpholine, dimethylethanolamine, N,N-dimethylbenzylamine, 1,8-diazabicyclo(5,4,0)undecene-7, isopropyl titanate, tetrabutyl titanate, oxyisoproply vanadate, n-propyl zirconate, and 1,4-diazabicyclo[2,2,2]octane. Polyisocyanate and polyol which are raw materials of a polyurethane resin are usually used as a monomer alone.

In the present invention, the viscosity of polyol which is a raw material of a polyurethane resin is preferably 1000 mPa·s or less, further preferably 800 mPa·s or less (B-type viscometer, 25° C., 12 rotation), and the viscosity of polyisocyanate is 300 mPa·s or less, further preferably 200 mPa·s or less (B-type viscometer, 25° C., 12 rotation).

A polyurea resin is a thermosetting resin made from liquid polyamine and liquid polyisocyanate as raw materials.

Examples of the polyisocyanate include the above-described polyisocyanates. Examples of the polyamine include diethylenetriamine, and triethylenetetramine.

A polyurethane-polyurea resin is a thermosetting resin made from polyisocyanate, polyol and polyamine as liquid raw materials.

In the present invention, a process of producing the coated pesticide will be described below using an example of the case where the thermosetting resin is a polyurethane resin.

A process of producing the coated pesticide in which the thermosetting resin is a polyurethane resin usually comprises steps of (1) mixing a powdery pesticide and polyol, (2) adding polyisocyanate to the mixture obtained in the previous step, (3) allowing polyol to react with polyisocyanate to produce a thermosetting resin to obtain an agglomerate in which the powdery pesticide is solidified with the polyurethane resin, and (4) adding polyol and polyisocyanate simultaneously or sequentially to the agglomerate of the powdery pesticide obtained in the previous step to react the polyol and the polyisocyanate, thereby coating the agglomerate with the polyurethane resin. In the step (1), usually, polyol is added to a powdery pesticide in the flowing or rolling state in a container to mix the powdery pesticide and the polyol in the container. In the step (2), usually, polyisocyanate is added to the mixture obtained in the previous step which is in the flowing or rolling state in the container. In the step (3), usually, the polyol and the polyisocyanate react to cure the polyurethane resin, while providing a suitable shearing force to the mixture obtained in the previous step by means of rotating blades or the like, and thereby the polyurethane resin intervenes between particles of the powdery pesticide to produce an agglomerate of the powdery pesticide. When the amount of the added polyurethane resin is small relative to the amount of the powdery pesticide, the steps (1) to (3) are appropriately repeated to obtain an agglomerate. Then, in the step (4), usually, polyol and polyisocyanate are simultaneously or sequentially added to the agglomerate obtained in the previous step while allowing the agglomerate to flow or roll in a container, and a suitable shearing force is provided to the resulting mixture by means of rotating blades or the like, thereby the polyol and the polyisocyanate react to coat the agglomerate with the polyurethane resin. In addition, the step (4) is repeated a plurality of times if necessary until a coating of the polyurethane resin having a suitable thickness is obtained.

In the process of producing the coated pesticide as described above, examples of the container for maintaining the powdery pesticide in the flowing or rolling state in the step (1) or the like include pan-type or a dram-type containers equipped with an appropriate stirring means. The steps (1) to (4) are performed in a nitrogen atmosphere usually at 0 to 100° C., and preferably at 10 to 80° C. In the step (3), the time required for the cure of a polyurethane resin varies depending on the operation temperature, the kinds of polyol and polyisocyanate, the presence or the absence of a curing catalyst, or the like. In the step (3), a shearing force is provided to a mixture of the powdery pesticide and an uncured polyurethane resin by means of rotating blades or the like to such an extent that an agglomerate having an appropriate particle diameter can be produced from the powdery pesticide by allowing the polyurethane resin to intervene between particles of the powdery pesticide. Specifically, the rotating speed of the blade at the tip portion is 50 to 3000 m/min, preferably 100 to 2000 m/min, more preferably 200 to 1000 m/min.

The total amount of polyol and polyisocyanate added in one operation at the step (1) and the step (2), or the step (4), that is, the amount of an uncured polyurethane resin varies depending on the kind of a polyurethane resin, the operation temperature, an instrument used or the like, and it is usually in the range of 0.3 to 15 parts by weight, preferably 0.5 to 10 parts by weight per 100 parts by weight of the powdery pesticide.

Specific examples of a container that can be used in the production process of the present invention include an apparatus in which particles circulate along the circumference of a container, such as NEW-GRA Machine (manufactured by Seishin Enterprise Co., Ltd.), and an apparatus comprising a low-speed rotation agitator in a mixer and a high-speed rotation chopper at a side portion, which can mix, disperse and shear loaded raw materials with the action of both blades in a short time, such as High Speed Mixer and High Flex Gral (manufactured by Fukae Powtec). Further examples of an apparatus having the similar performance include High Speed Mixer (manufactured by Freund), Vertical Granulator (manufactured by Powlex Corporation), and New Speed Mill (manufactured by Okada Seiko Co., Ltd.). Specific examples thereof include the apparatus described in JP-A 9-75703.

The amount of the thermosetting resin to be contained in the coated pesticide is usually 5 to 150 parts by weight, preferably 10 to 100 parts by weight, more preferably 20 to 80 parts by weight per 100 parts by weight of the powdery pesticide.

In the present invention, the coated pesticide is a powder having a volume median diameter of 10 to 150 µm, preferably a powder having a volume median diameter of 10 to 80 µm.

The shape of the coated pesticide is usually almost spherical. The bulk density of the coated pesticide is preferably 1.0 g/ml or less, more preferably 0.6 g/ml or less.

Although calcium carbonate is roughly classified into two kinds of heavy calcium carbonate and precipitated calcium carbonate depending on its production process, the calcium carbonate micropowder having a bulk density of 0.6 g/ml or less in the powdery pesticidal composition of the present invention may be any calcium carbonate.

Heavy calcium carbonate is also called natural calcium carbonate, and is produced by mechanically dry- or wet-grinding and classifying a natural raw material containing $CaCO_3$ as the main component such as limestone, shell exoskeleton or chalk.

Precipitated calcium carbonate is also called synthetic calcium carbonate, and is produced by a carbonic acid gas method which comprises dissolving calcined lime obtained by firing limestone in water to obtain lime milk, and then blowing carbonic acid gas into the lime milk, or a soluble salt reaction method which comprises allowing calcium chloride or lime milk to react with soda ash in water.

The calcium carbonate used in the present invention usually has a specific surface area of 1 to 100 $m^2/g$, preferably 0.5 to 50 $m^2/g$. The specific surface area of calcium carbonate can be measured, for example, by the BET method (a method which comprises adsorbing an inert gas molecule such as nitrogen, wherein the area occupied by the adsorption of the molecule is known, onto the surface of a powder particle at the temperature of liquid nitrogen, and calculating the specific surface area of a sample from the adsorption amount of the molecule).

The calcium carbonate used in the present invention has a bulk density of 0.6 g/ml or less, preferably a bulk density in the range of 0.01 to 0.3 g/ml. In the present invention, a bulk density is measured according to the "Physical Property Testing Method" of Ministry of Agriculture and Forestry Notification (Feb. 3, 1960, Ministry of Agriculture and Forestry Notification No. 71). Specifically, a bulk density is measured, for example, by the following method.

A standard sieve (opening 0.175 mm) is placed on a metal cylindrical container having a volume of 100 ml and a diameter of 50 mm so that the distance between the net of the sieve and the upper edge of the container can be kept at 20 cm. A measurement sample is sieved, and is filled into the container. Immediately, the excess sample is removed using a slide glass, and the filled container is weighed to calculate the weight (g) of the content. Then, a bulk density is calculated by the following calculation equation:

Bulk density (g/ml)=weight (g) of content/100 (ml).

The powdery pesticidal composition of the present invention is obtained by mixing the coated pesticide and the calcium carbonate, and the weight ratio of the coated pesticide and the calcium carbonate is in the range of 100:1 to 100:30, preferably in the range of 100:2 to 100:20, more preferably in the range of 100:4 to 100:15.

The powdery pesticidal composition of the present invention can be easily prepared by mixing the coated pesticide and the calcium carbonate in a container equipped with a stirring means. Examples of the container equipped with a stirring means include the above-described containers used in the process for producing the coated pesticide. In the production of the coated pesticide, after a coating of the thermosetting resin is completely cured, a predetermined amount of calcium carbonate can be added to and mixed with the coated pesticide to prepare the powdery pesticidal composition of the present invention.

The powdery pesticidal composition of the present invention obtained by uniformly mixing a predetermined amount of calcium carbonate with the coated pesticide has good flowability as a powder body. For example, it is easy to discharge the powdery pesticidal composition from a stirrer which is used in the production of the coated pesticide, and bridging is hardly generated when the powdery pesticidal composition is discharged from a container such as a hopper. In addition, when the powdery pesticidal composition of the present invention is directly sprayed to pests to be controlled or plants or soil to be protected, a normal duster such as a powder duster can be used. In addition, the powdery pesticidal composition of the present invention can be mixed with an pesticidally active compound different from the pesticidally active compound contained in the coated pesticide, if necessary, and then used.

EXAMPLES

The present invention will be described in more detail by way of the following Examples which the present invention is not limited to.

Reference Example 1 (Preparation of Coated Pesticide 1)

Preparation of Powdery Pesticide 1:
70.0 parts by weight of (E)-1-(2-chloro-1,3-thiazol-5-ylmethyl)-3-methyl-2-nitroguanidine (common name: clothianidine) and 30.0 parts by weight of Shokozan Clay S (manufactured by Shokozan Mining Co., Ltd.) were uniformly mixed. The total amount of the mixture was ground with a centrifugation grinding machine to obtain a powdery pesticide having a volume median diameter of 15.0 μm (MASTERSIZER2000 manufactured by MALVERN Instruments Ltd.) and containing (E)-1-(2-chloro-1,3-thiazol-5-ylmethyl)-3-methyl-2-nitroguanidine (hereinafter, referred to as the powdery pesticide 1).
Preparation of Polyol Premix 1
56.1 parts by weight of SUMIPHEN™ (branched polyether polyol manufactured by Sumika Bayer Urethane Co., Ltd.), 42.3 parts by weight of SUMIPHEN 1600U (linear polyether polyol manufactured by Sumika Bayer Urethane Co., Ltd.) and 1.6 parts by weight of 2,4,6-tris(dimethylaminomethyl)phenol (manufactured by Kayaku Akzo Corporation) were uniformly mixed to obtain a liquid mixture of polyol and a catalyst (hereinafter, referred to as the polyol premix 1). The viscosity of the polyol premix 1 was 364 m·Pa (B-type viscometer, 25° C., 12 rotation, rotor No. 1).
Preparation of Coated Pesticide 1
Into a container of High Speed Mixer apparatus (Model LFS-GS-1J manufactured by Fukae Powtec; an apparatus having agitator blades whose rotation axis is a vertical line passing through the center of the bottom of a round dish-type container part, and chopper blades whose rotation axis is a horizontal line penetrating through the side surface of the round dish-type container part) was loaded 100 parts by weight of the powdery pesticide 1, and the agitator blades (rotation number: 850 rpm) and the chopper blades (rotation number: 3500 rpm) of the apparatus were rotated. Then, the mixing container was warmed, and 1.86 parts by weight of the polyol premix 1 was added thereto while the temperature of the powdery pesticide 1 was kept at 75±5° C. It was observed that the powdery pesticide 1 was wetted with the polyol premix 1. After 3 minutes, 1.14 parts by weight of SUMIDUR 44V10 (polymethylenepolyphenyl polyisocyanate manufactured by Sumika Bayer Urethane Co., Ltd., viscosity 130 m·Pa (25° C.)) was added thereto while the temperature of a product was kept at 75±5° C. From immediately after addition, a phenomenon of viscosity increasing was observed. Thereafter, the viscosity was reduced, and curing of a polyurethane resin was observed (corresponding to 3.0 parts by weight of a polyurethane resin per 100 parts by weight of the powdery pesticide 1). After 5 minutes, the following operation was repeated 19 times while the temperature of a product was kept at 75±5° C.

Addition of 1.86 parts by weight of the polyol premix 1→Wait for 3 minutes→Addition of 1.14 parts by weight of SUMIDUR 44V10→Wait for 5 minutes.

During the above-described operation, the High Speed Mixer apparatus continued stirring and mixing capable of providing a shearing force under the same conditions.

A total of 60 parts by weight of the raw materials of the polyurethane resin were added per 100 parts by weight of the powdery pesticide 1. The mixing container was cooled to obtain the coated pesticide 1 (addition time of raw materials of polyurethane resin: 20 times, addition amount of raw materials of polyurethane resin per one time: 3.0 parts by weight, total addition amount of raw materials of polyurethane resin: 60 parts by weight, volume median diameter: 75 μm, bulk density: 0.41 g/ml).

Reference Example 2 (Preparation of Coated Pesticide 2)

Preparation of Powdery Pesticide 2
45.5 parts by weight of 5-chloro-N-(1,3-dihydro-1,1,3-trimethyl-4-isobenzofuranyl)-1,3-dimethylpyrazole-4-carboxamide (common name: furametpyr), 9 parts by weight of Tokusil GU-L (hydrous amorphous silicon dioxide manufactured by Tokuyama Corporation) and 45.5 parts by weight of Bentonite Fuji (manufactured by Hojun) were uniformly mixed. The total amount of the mixture was ground with a centrifugation grinding machine to obtain a powdery agrichemical having a volume median diameter of 5.0 μm (MASTERSIZER2000 manufactured by MALVERN Instruments Ltd.) and containing 5-chloro-N-(1,3-dihydro-1,1,3-trimethyl-4-isobenzofuranyl)-1,3-dimethylpyrazole-4-carboxamide (hereinafter, referred to as the powdery pesticide 2).
Preparation of Coated Pesticide 2
Into a container of High Speed Mixer apparatus (Model LFS-GS-1J manufactured by Fukae Powtec; an apparatus having agitator blades whose rotation axis is a vertical line passing through the center of the bottom of a round dish-type container part, and chopper blades whose rotation axis is a horizontal line penetrating through the side surface of the round dish-type container part) was loaded 100 parts by weight of the powdery pesticide 2, and the agitator blades (rotation number: 850 rpm) and the chopper blades (rotation number: 3500 rpm) of the apparatus were rotated. Then, the mixing container was warmed, and 1.86 parts by weight of the polyol premix 1 was added thereto while the temperature of the powdery pesticide 2 was kept at 75±5° C. It was observed that the powdery pesticide 2 was wetted with the polyol premix 1. After 3 minutes, 1.14 parts by weight of SUMIDUR 44V10 (polymethylenepolyphenyl polyisocyanate manufactured by Sumika Bayer Urethane Co., Ltd., viscosity 130 m·Pa (25° C.)) was added thereto while the temperature of a product was kept at 75±5° C. From immediately after addition, a phenomenon of viscosity increasing was observed. Thereafter, the viscosity was reduced, and curing of a polyurethane resin was observed (corresponding to 3.0 parts by weight of a polyurethane resin per 100 parts by weight of the powdery pesticide). After 5 minutes, the following operation was repeated 6 times while the temperature of a product was kept at 75±5° C.

Addition of 1.86 parts by weight of the polyol premix 1→Wait for 3 minutes→Addition of 1.14 parts by weight of SUMIDUR 44V10→Wait for 5 minutes.

During the above-described operation, the High Speed Mixer apparatus continued stirring and mixing capable of providing a shearing force under the same conditions.

A total of 21 parts by weight of the raw materials of the polyurethane resin were added per 100 parts by weight of the powdery pesticide 2. The mixing container was cooled to obtain the coated pesticide 2 (addition time of raw materials of polyurethane resin: 7 times, addition amount of raw materials of polyurethane resin per one time: 3.0 parts by weight, total addition amount of raw materials of polyurethane resin: 21 parts by weight, volume median diameter: 40 μm, bulk density: 0.37 g/ml).

Reference Example 3 (Preparation of Coated Pesticide 3)

Preparation of Powdery Pesticide 3

65 parts by weight of (E)-N-(6-chloro-3-pyridylmethyl)-N-ethyl-N'-methyl-2-nitrovinylidenediamine (common name: nitenpyram) and 35 parts by weight of Shokozan Clay S (kaolin clay: manufactured by Shokozan Mining Co., Ltd.) were uniformly mixed. The total amount was ground with a centrifugation grinding machine to obtain a powdery agrichemical having a volume median diameter of 16.0 μm (MASTERSIZER2000 manufactured by MALEVRN Instruments Ltd.) and containing (E)-N-(6-chloro-3-pyridylmethyl)-N-ethyl-N'-methyl-2-nitrovinylidenediamine (hereinafter, referred to as the powdery pesticide 3).

Preparation of Coated Pesticide 3

Into a container of High Speed Mixer apparatus (Model LFS-GS-1J manufactured by Fukae Powtec; an apparatus having agitator blades whose rotation axis is a vertical line passing through the center of the bottom of a round dish-type container part, and chopper blades whose rotation axis is a horizontal line penetrating through the side surface of the round dish-type container part) was loaded 100 parts by weight of the powdery pesticide 3, and the agitator blades (rotation number: 1800 rpm) and the chopper blades (rotation number: 2000 rpm) of the apparatus were rotated. Then, the mixing container was warmed, and 1.55 parts by weight of the polyol premix 1 was added thereto while the temperature of the powdery pesticide 3 was kept at 75±5° C. It was observed that the powdery pesticide 3 was wetted with the polyol premix 1. After 3 minutes, 0.95 parts by weight of SUMIDUR 44V10 (polymethylenepolyphenyl polyisocyanate manufactured by Sumika Bayer Urethane Co., Ltd., viscosity 130 m·Pa (25° C.)) was added thereto while the temperature of a product was kept at 75±5° C. From immediately after addition, a phenomenon of viscosity increasing was observed. Thereafter, the viscosity was reduced, and curing of a polyurethane resin was observed (corresponding to 2.5 parts by weight of a polyurethane resin per 100 parts by weight of the powdery pesticide). After 5 minutes, the following operation was repeated 19 times while the temperature of a product was kept at 75±5° C.

Addition of 1.55 parts by weight of the polyol premix 1→Wait for 3 minutes→Addition of 0.95 parts by weight of SUMIDUR 44V10→Wait for 5 minutes.

During the above-described operation, the High Speed Mixer apparatus continued stirring and mixing capable of providing a shearing force under the same conditions.

A total of 50 parts by weight of the raw materials of the polyurethane resin were added per 100 parts by weight of the powdery pesticide 3. The mixing container was cooled to obtain the coated pesticide 3 (addition time of raw materials of polyurethane resin: 20 times, addition amount of raw materials of polyurethane resin per one time: 2.5 parts by weight, total addition amount of raw materials of polyurethane resin: 50 parts by weight, volume median diameter: 53 μm).

Preparation Examples 1 to 12 and Comparative Examples 1 to 6 (Preparation of Powdery Composition)

The coated pesticide 1 prepared in Reference Example 1 and a micropowder described in the following Table 1 were charged into a container of High Speed Mixer apparatus (Model LFS-GS-1J manufactured by Fukae Powtec) at the weight ratio described in Table 1. The materials were stirred and mixed by rotating agitator blades (rotation number: 850 rpm) and chopper blades (rotation number: 3500 rpm) of the apparatus for 5 minutes to prepare a powdery composition.

TABLE 1

| | Micropowder | Apparent specific gravity (g/ml) | Coated pesticide 1:micropowder (weight ratio) |
|---|---|---|---|
| Production Example 1 | Calcium carbonate (*1) | 0.25 | 100:4 |
| Production Example 2 | Calcium carbonate (*1) | 0.25 | 100:7 |
| Production Example 3 | Calcium carbonate (*1) | 0.25 | 100:10 |
| Production Example 4 | Calcium carbonate (*2) | 0.24 | 100:4 |
| Production Example 5 | Calcium carbonate (*2) | 0.24 | 100:7 |
| Production Example 6 | Calcium carbonate (*2) | 0.24 | 100:10 |
| Production Example 7 | Calcium carbonate (*3) | 0.38 | 100:4 |
| Production Example 8 | Calcium carbonate (*3) | 0.38 | 100:7 |
| Production Example 9 | Calcium carbonate (*3) | 0.38 | 100:10 |
| Production Example 10 | Calcium carbonate (*4) | 0.53 | 100:4 |
| Production Example 11 | Calcium carbonate (*4) | 0.53 | 100:7 |
| Production Example 12 | Calcium carbonate (*4) | 0.53 | 100:10 |
| Comparative Example 1 | Pyrophyllite (*5) | 0.65 | 100:4 |
| Comparative Example 2 | Pyrophyllite (*5) | 0.65 | 100:7 |
| Comparative Example 3 | Pyrophyllite (*5) | 0.65 | 100:10 |
| Comparative Example 4 | Calcium carbonate (*6) | 0.91 | 100:4 |
| Comparative Example 5 | Calcium carbonate (*6) | 0.91 | 100:7 |

TABLE 1-continued

| | Micropowder | Apparent specific gravity (g/ml) | Coated pesticide 1:micropowder (weight ratio) |
|---|---|---|---|
| Comparative Example 6 | Calcium carbonate (*6) | 0.91 | 100:10 |

(*1): Light calcium carbonate (manufactured by Maruo Calcium Co., Ltd.)
(*2): Heavy calcium carbonate NS#2300 (manufactured by Nitto Funka Kogyo K.K.)
(*3): Heavy calcium carbonate NS#400 (manufactured by Nitto Funka Kogyo K.K.)
(*4): Heavy calcium carbonate SS#80 (manufactured by Nitto Funka Kogyo K.K.)
(*5): Shokozan Clay S (hydrous aluminum silicate; manufactured by Shokozan Mining Co., Ltd.)
(*6): Heavy calcium carbonate NN#200 (manufactured by Nitto Funka Kogyo K.K.)

Then, flowability of the above-prepared pesticidal compositions was assessed by the following test method. Each test result is described in Table 2.

Here, the test was performed using a powder tester Model PT-D (manufactured by Hosokawa Micron Group).

Test Example 1 (Spatula Angle)

A vat was placed on a ramp for measuring a spatula angle, and a sample was added thereto until the spatula was hidden. The ramp was calmly lowered, and a tilt angle of a side surface of the sample accumulated on the spatula was measured (tilt angle 1). Then, an attached bell was used to make an impact on the spatula, and a tilt angle of a side surface of the sample accumulated on the spatula was measured (tilt angle 2). An average of the tilt angle 1 and the tilt angle 2 was adopted as a spatula angle.

TABLE 2

| | Tilt angle 1 (degree) | Tilt angle 2 (degree) | Average (degree) |
|---|---|---|---|
| Only coated pesticide 1 | 90 | 90 | 90 |
| Production Example 1 | 80 | 65 | 73 |
| Production Example 2 | 64 | 46 | 55 |
| Production Example 3 | 60 | 50 | 55 |
| Production Example 4 | 70 | 50 | 60 |
| Production Example 5 | 59 | 47 | 53 |
| Production Example 6 | 50 | 42 | 46 |
| Production Example 7 | 70 | 56 | 63 |
| Production Example 8 | 64 | 50 | 57 |
| Production Example 9 | 55 | 44 | 50 |
| Production Example 10 | 76 | 60 | 68 |
| Production Example 11 | 72 | 54 | 63 |
| Production Example 12 | 62 | 49 | 56 |
| Comparative Example 1 | 90 | 82 | 86 |
| Comparative Example 2 | 90 | 82 | 86 |
| Comparative Example 3 | 90 | 62 | 76 |
| Comparative Example 4 | 90 | 76 | 83 |
| Comparative Example 5 | 90 | 80 | 85 |
| Comparative Example 6 | 90 | 64 | 77 |

INDUSTRIAL APPLICABILITY

The powdery pesticidal composition of the present invention has good flowability as a powder, and is useful as a composition containing a coated pesticide in which a powdery pesticide is coated with a thermosetting resin.

The invention claimed is:

1. A powdery pesticidal composition comprising a mixture of a coated pesticide having a volume median diameter of 10 to 150 μm in which a powdery agrichemical is coated with a themosetting resin, and a calcium carbonate micropowder having a bulk density of 0.6 g/ml or less, wherein the weight ratio of the coated pesticide to the calcium carbonate micropowder is in the range of 100:1 to 100:30.

2. The powdery pesticidal composition according to claim 1, wherein the thermosetting resin is a polyurethane resin and/or a polyurea resin.

3. The powdery pesticidal composition according to claim 1 or 2, wherein the bulk density of the calcium carbonate micropowder is in the range of 0.01 to 0.3 g/ml.

4. A method for improving flowability of a powdery coated pesticide which comprises adding a calcium carbonate micropowder having a bulk density of 0.6 g/ml or less to a powdery coated pesticide in which a powdery pesticide is coated with a thermosetting resin, in such an amount that the weight ratio of the powdery coated pesticide and the calcium carbonate micropowder is in the range of 100:1 to 100:30.

* * * * *